(12) United States Patent
Klopman et al.

(10) Patent No.: US 8,518,990 B2
(45) Date of Patent: *Aug. 27, 2013

(54) CANCER TREATMENT

(75) Inventors: Gilles Klopman, Sarasota, FL (US); Suman K. Chakravarti, Beachwood, OH (US)

(73) Assignee: Oncophor, LLC, Beachwood, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/247,171

(22) Filed: Sep. 28, 2011

(65) Prior Publication Data

US 2012/0065208 A1 Mar. 15, 2012

Related U.S. Application Data

(63) Continuation-in-part of application No. 12/723,911, filed on Mar. 15, 2010.

(60) Provisional application No. 61/387,176, filed on Sep. 28, 2010, provisional application No. 61/159,832, filed on Mar. 13, 2009.

(51) Int. Cl.

| | |
|---|---|
| *A01N 37/30* | (2006.01) |
| *A01N 33/02* | (2006.01) |
| *A01N 33/18* | (2006.01) |
| *A01N 33/24* | (2006.01) |
| *A61K 31/205* | (2006.01) |
| *A61K 31/135* | (2006.01) |
| *A61K 31/04* | (2006.01) |

(52) U.S. Cl.
USPC ............................ 514/554; 514/646; 514/741

(58) Field of Classification Search
None
See application file for complete search history.

(56) References Cited

PUBLICATIONS

Stevens et al. "The hyperproliferative endothelial cell phenotype in idiopathic pulmonary arterial hypertension", Am.J.Physiol.LungCell.Mol.Physiol., 2007, vol. 293, pp. L546-L547.*
Hipfner, "Connecting Proliferation and Apoptosis in Development and Disease", Nat.Rev.Mol.CellBio., 2004, vol. 5, pp. 805-815.*
Neidle, Cancer Drug Design and Discovery, Elsevier/Academic Press, 2008, pp. 427-431.*

* cited by examiner

*Primary Examiner* — James D Anderson
*Assistant Examiner* — Stephanie Springer
(74) *Attorney, Agent, or Firm* — Fay Sharpe LLP

(57) ABSTRACT

A method for treating, preventing or ameliorating a hyperliferative disease and/or disorder in a mammal, comprises administering a therapeutically effective amount of one or more compounds selected from the group consisting of a compound of Formula (III), a compound of Formula (IV), and a pharmaceutically acceptable salt of Formula (III) or Formula (IV):

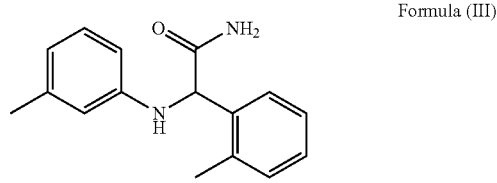

Formula (III)

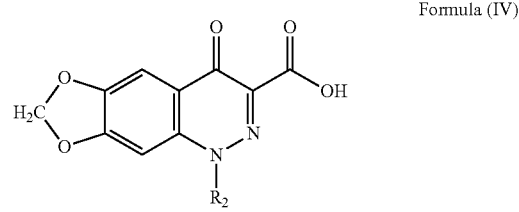

Formula (IV)

wherein $R_2$ is selected from the group consisting of methyl, ethyl, n-propyl, isopropyl, n-butyl, vinyl and allyl.

11 Claims, 2 Drawing Sheets

CANCER TREATMENT

This application claims the priority benefit of U.S. Provisional Patent Application Ser. No. 61/387,176, filed Sep. 28, 2010. This application is also a continuation-in-part of U.S. patent application Ser. No. 12/723,911, filed Mar. 15, 2010. U.S. patent application Ser. No. 12/723,911 claimed the priority benefit of U.S. Provisional Patent Application Ser. No. 61/159,832, filed Mar. 13, 2009. The disclosures of these applications are incorporated herein by reference.

BACKGROUND

The present exemplary embodiment relates to the discovery of new chemicals that can be used for the treatment, prevention, or amelioration of hyperproliferative diseases and/or disorders, such as cancer. It finds particular application in conjunction with a computer based methodology for identifying new chemical compositions, and will be described with particular reference thereto. However, it is to be appreciated that the present exemplary embodiment is also amenable to other like applications.

Cancer is a class of diseases in which groups of cells display uncontrolled growth, intrusion and destruction of adjacent tissues, and sometimes spread to other locations in the body. Cancer treatments are generally designed to slow the progress of the cancer or eliminate it entirely. Various treatments include radiation therapy, immunotherapy, hormonal therapy, gene therapy, chemotherapy, targeted therapy and surgical procedures. All of these approaches pose significant drawbacks for the patient. Surgery, for example, may be contraindicated due to the health of the patient or may be unacceptable to the patient. Additionally, surgery may not completely remove the neoplastic tissue. Radiation therapy is only effective when the neoplastic tissue exhibits a higher sensitivity to radiation than normal tissue, and radiation therapy can also often elicit serious side effects. Hormonal therapy is rarely given as a single agent and although can be effective, is often used to prevent or delay recurrence of cancer after other treatments have removed the majority of the cancer cells. Biological therapies/immunotherapies are limited in number and may produce side effects such as rashes or swellings, flu-like symptoms, including fever, chills and fatigue, digestive tract problems or allergic reactions.

Many potential drugs have been discovered in the last 30 years for treating cancer. In fact, a large number of different cancers are treated successfully and produce strong remissions that often prevent the cancers of regaining strength. The mechanisms by which these results are obtained are to kill the cells by interfering with the reproductive machinery of cell replication. For example, standard cancer chemotherapeutic drugs kill cancer cells upon induction of programmed cell death ("apoptosis") by targeting basic cellular processes and molecules. These basic cellular processes and molecules include RNA/DNA (alkylating and carbamylating agents, platin analogs and topoisomerase inhibitors), metabolism (drugs of this class are named anti-metabolites and examples are folic acid, purin and pyrimidine antagonist) as well as the mitotic spindle apparatus with $\alpha\beta$-tubulin heterodimers as the essential component (drugs are categorized into stabilizing and destabilizing tubulin inhibitors; examples are Taxol/Paclitaxel®, Docetaxel/Taxotere® and vinca alkaloids). A significant majority of cancer chemotherapeutics act by inhibiting DNA synthesis, either directly, or indirectly by inhibiting the biosynthesis of the deoxyribonucleotide triphosphate precursors, to prevent DNA replication and concomitant cell division. These agents, which include alkylating agents, such as nitrosourea, anti-metabolites, such as methotrexate and hydroxyurea, and other agents, such as etoposides, campathecins, bleomycin, doxorubicin, daunorubicin, etc., although not necessarily cell cycle specific, kill cells during S phase because of their effect on DNA replication. Other agents, specifically colchicine and the vinca alkaloids, such as vinblastine and vincristine, interfere with microtubule assembly resulting in mitotic arrest.

Despite the availability of a variety of chemotherapeutic agents, chemotherapy has many drawbacks. Almost all chemotherapeutic agents are toxic, and chemotherapy causes significant, and often dangerous, side effects, including severe nausea, bone marrow depression, immunosuppression, etc. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even those agents that act by mechanisms different from the mechanisms of action of the drugs used in the specific treatment; this phenomenon is termed pleiotropic drug or multidrug resistance. Thus, because of drug resistance, many cancers prove refractory to standard chemotherapeutic treatment protocols.

Because some of these drugs are carefully designed to interfere with the replication of fast growing cells, they also often interfere with the replication of those non-carcinogenic cells that also constantly replicate, such as hair, gut lining and so on. As a result, these drugs have to be used at low doses in order to minimize the terrifying effects of the treatments. The challenge is therefore how to create potent and specific cancer cells killing agents, or inhibiting agents with minimal side effects, and, notably without killing other reproducing cells.

The Mcase program was originally developed and is presently widely used by regulatory agencies and pharmaceutical research companies to replace laboratory animals in the evaluation of the potential toxic effect of chemicals. The program is based on hierarchical statistical analysis of a database (a training set) composed of a number of chemicals with their biological activity data. The program aims to discover substructures that appear mostly in active molecules and may therefore be responsible for the observed activity. The Mcase program begins by identifying the most statistically significant substructure existing within the learning set. This fragment is labeled a biophore, and is responsible for the activity of the largest possible number of active molecules. The active molecules containing this biophore are then removed from the database, and the remaining ones are submitted to a new analysis leading to the identification of the next biophore. This procedure is repeated until either the activity of all the molecules in the learning set have been accounted for or no additional statistically significant substructure can be found. For each set of molecules containing a specific biophore, Mcase identifies additional parameters, deemed modulators, which can be used in the construction of a quantitative structure-activity relationship within this reduced set of congeneric molecules. Modulators consist of the presence of certain substructures or the value of calculated parameters, such as the highest occupied and lowest unoccupied orbital energies, octanol-water partition coefficient and so on. The process is automated and proceeds with minimal human intervention and bias. The knowledge that the program gains during the training process can then be used to predict the biological activity of new chemicals that were not included in the training set.

Advantageously, the present disclosure provides a method for identifying new chemical compositions that are active for treating, preventing or ameliorating hyperproliferative disease and/or disorders such as cancer with minimal or none of the side effects often associated with chemotherapy. By not killing normally reproducing cells, drugs which do not exhibit high potency can be used in large doses that might still be sufficient to realize the medical objective. However, while the concept is simple, the realization is elusive and has not been achieved so far in a rational and meaningful way.

BRIEF DESCRIPTION

According to a first aspect, a compound is provided for treating, preventing, or ameliorating a hyperproliferative disease and/or disorder in a mammal. The compound is selected from the group consisting of Formula (III) and Formula (IV)

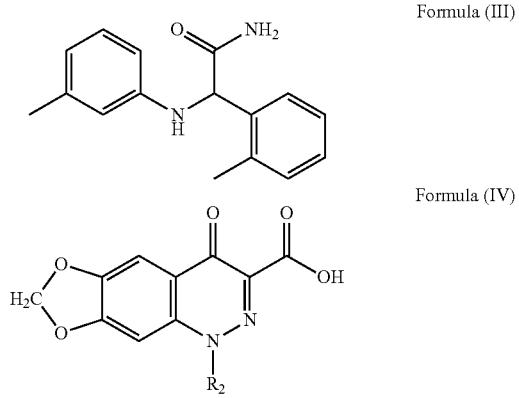

wherein $R_2$ is selected from the group consisting of methyl, ethyl, n-propyl, isopropyl, n-butyl, vinyl and allyl.

According to a second aspect, a compound is provided for treating, preventing, or ameliorating a hyperproliferative disease and/or disorder in a mammal comprising Formula (III) or a pharmaceutically acceptable salt thereof.

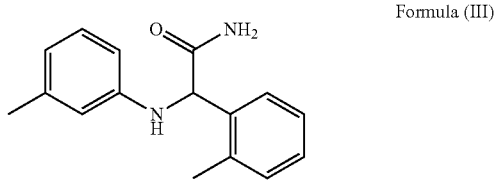 [SMILES: Cc1cccc(NC(C(N)=O)c2ccccc2C)c1]

According to a third aspect, a process for evaluating new chemicals active against cancer, but without detrimental side effects commonly observed during traditional chemotherapy. The process comprises identifying the statistically most significant substructures located within the chemicals, constructing a quantitative structure-activity relationship within the substructures, and predicting biological activity of new chemicals based on the constructed relationship within the substructures

DETAILED DESCRIPTION

Figure 1:
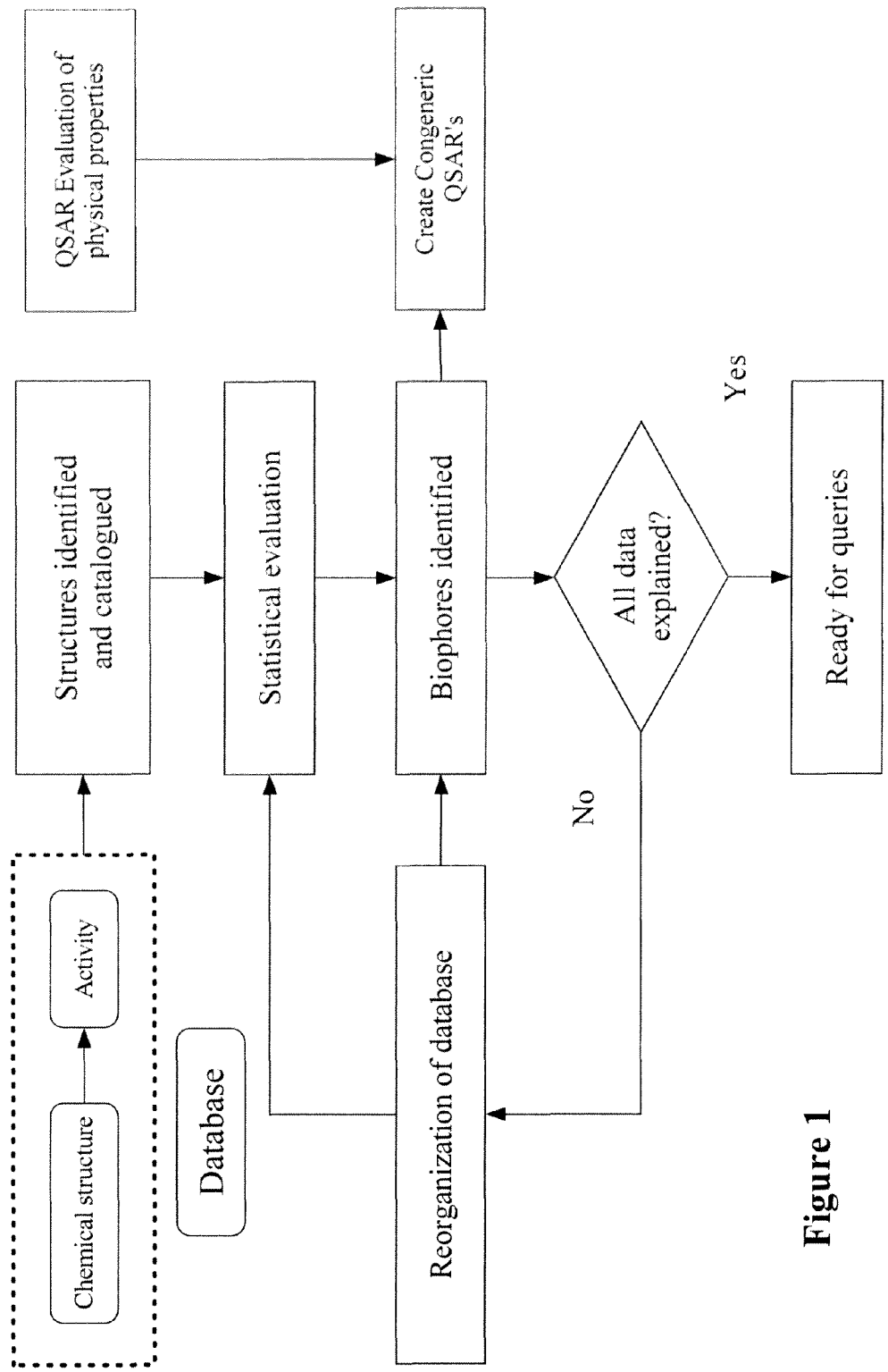
FIG. 1 illustrates one exemplary Mcase operation process using MC4PC, which is a statistical/correlative program containing predefined predictive modules for mutagenicity, carcinogenicity, and teratogenicity. MC4PC is essentially a Windows based PC version of Mcase. All the calculations may be performed using a processor, such as an Intel Pentium III processor.
Figure 2:
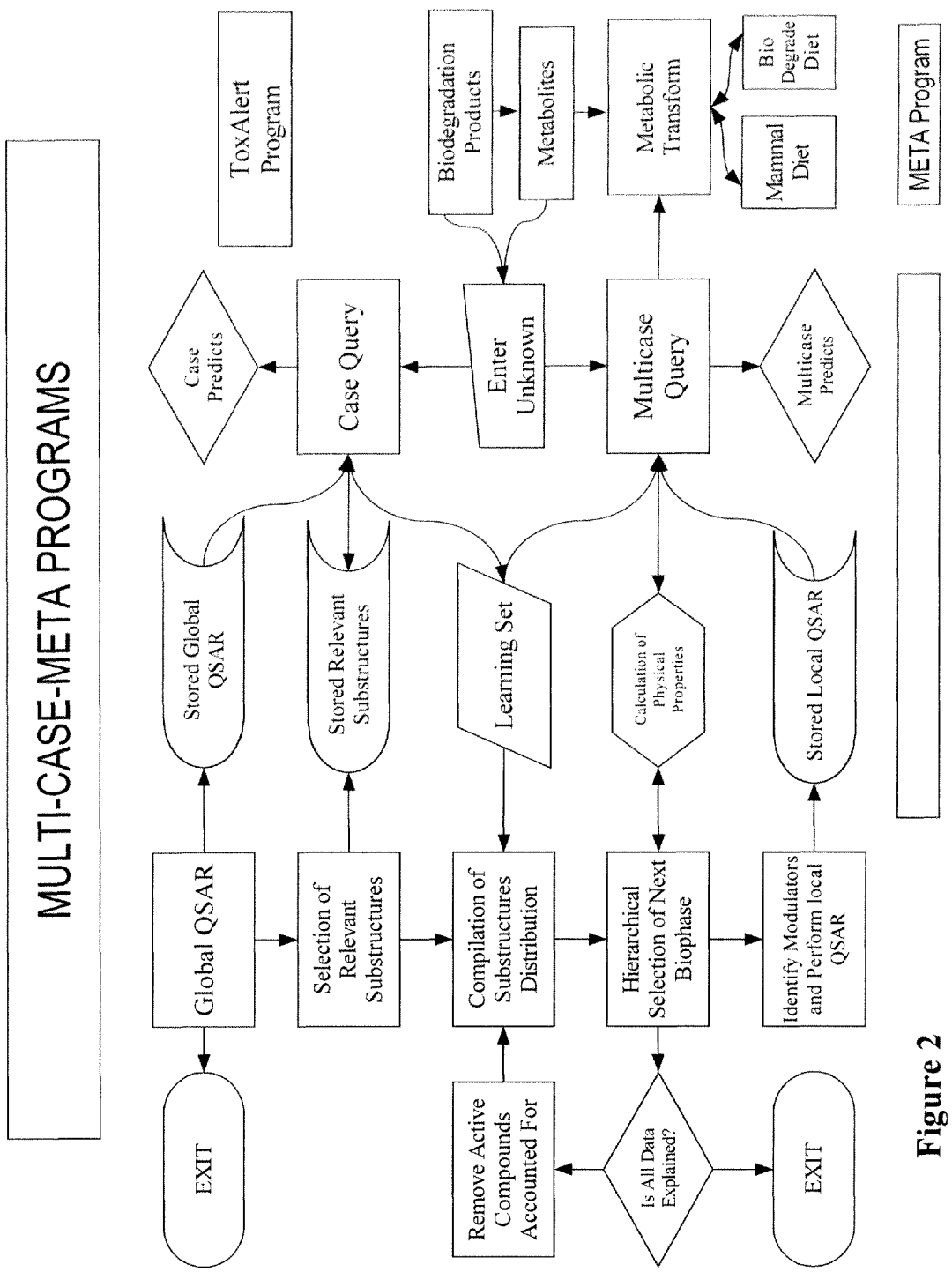
FIG. 2 further exemplifies the Mcase methodology and how this process can be used concurrently with the Case and META programs. Initially, the META program analyzes known chemical compositions and predicts potential metabolic transformations, biodegradation products, metabolites, and the like, that may be produced when the molecules are ingested or otherwise exposed to the environment. This program interfaces with the Mcase program, which can then further evaluate the potential toxicological and/or beneficial effects of the identified composition, and organize the data obtained. The Mcase program performs a number of queries, evaluating the molecule against the dictionaries and appropriate stored QSARs. Based on the results, Mcase ventures a prediction as to the projected activity of the molecule, and identifies a learning set that includes a compilation of substructures. The Mcase program then hierarchically selects biophores based on particular properties. The selected biophors are then analyzed to identify modulators and perform QSAR analysis. If all the data is explained and accounted for, the program is over; however if data remains unexplained, the active compounds that are accounted for are removed and the compilation of substructures is repeated until all the data is explained. Mcase may be used in conjunction with CASE-TOX, which uses the prediction modules developed by the Mcase/MC4PC programs to study toxic endpoints.

As used herein, the term "pharmaceutically acceptable" means approved by a regulatory agency of the Federal or a state government or listed in the U.S. Pharmacopeia or other generally recognized pharmacopeia for use in animals, and more particularly in humans.

As used herein, a "therapeutically effective amount" refers to that amount of the therapeutic agent sufficient to destroy, modify, control or remove a hyperproliferative disease and/or disorder such as primary, regional or metastatic cancer tissue. A therapeutically effective amount may refer to the amount of therapeutic agent sufficient to delay or minimize the spread of cancer. A therapeutically effective amount may also refer to the amount of the therapeutic agent that provides a therapeutic benefit in the treatment or management of cancer. Further, a therapeutically effective amount with respect to a therapeutic agent means that amount of therapeutic agent alone, or in combination with other therapies, that provides a therapeutic benefit in the treatment or management of cancer, including the amelioration of symptoms associated with the disease being treated.

In accordance with various aspects of the present disclosure, a MultiCASE (Mcase) software program is provided for use in the evaluation of the potential new chemicals that are active against various kinds of cancer. As described above, the Mcase program automatically evaluates a data set and tries to identify the structural features responsible for activity, called biophores. It then creates organized dictionaries of these biophores and develops ad hoc local quantitative structure-activity relationship (QSAR) correlations that can be used to predict the activity of known molecules.

Data for more than 500 databases of interest for the assessment of the safety of chemicals, foods and of environmental impact has been accumulated and assembled over the years. Information encoded in the NCI-60, available on the Internet from the National Cancer Institute is also included in the program. It is an object of the present disclosure to couple the Mcase program with the NCI-60 to identify chemicals possessing useful pharmaceutical properties (i.e. anti-cancer) named "oncophors (formally "biophors"), while devoid of adverse "biophobe" effects.

The Mcase program starts by identifying the statistically most significant biophores existing within the learning set. Theses biophors, are seen as being responsible for the high activity of the majority of active compounds, unless deactivated by biophobes, identified as documented fragments, preventing otherwise activity of otherwise active compounds.

Upon entering a new molecule, the Mcase program evaluates it against the dictionary and the appropriate QSARs it has created and, based on the results, ventures a prediction as to the projected activity of the molecule in the corresponding test. All conclusions and predictions may be documented and rationalized by querying the program. If the activity of the molecule is known, its observed value will also be displayed.

A model is created from the available chemicals and activities listed for the cell lines of a particular type of cancer. For each set of molecules containing a specific oncophor, Mcase identifies additional parameters, deemed modulators, which can be used in the construction of a QSAR within this reduced set of congeneric molecules. The identified modulators may include the presence of certain substructures or calculated parameters such HOMO and LUMO energies, octanol/water partition coefficient, and so on. The process involved is mostly automated and proceeds with minimal human intervention and bias. The program is able to accumulate knowledge during the training process, which can then be used to predict the biological activity of new chemicals that were not originally included in the training set.

Beginning with known chemical structures and activities in a database, the substructures of the chemical structures may be identified and catalogued. A statistical evaluation is performed to identify which of the identified substructures qualify as biophores. Simultaneously, a QSAR evaluation of physical properties is performed, and, together with the identified biophores, creates a congeneric QSAR. If all the data is not explained at this point, the database may be reorganized and the statistical evaluation may be repeated to account for any remaining data. Once all of the data is properly explained and accounted for, the program is ready for queries.

Disclosed in some embodiments is a method for treating, preventing or ameliorating a hyperliferative disease and/or disorder in a mammal. The method comprises administering a therapeutically effective amount of one or more compounds selected from the group consisting of a compound of Formula (III), a compound of Formula (IV), and a pharmaceutically acceptable salt or metabolite of Formula (III) or Formula (IV):

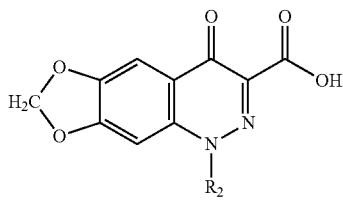

Formula (IV)

wherein $R_2$ is selected from the group consisting of methyl, ethyl, n-propyl, isopropyl, n-butyl, vinyl and allyl.

In some embodiments, $R_2$ in the compound of Formula (IV) is ethyl. This compound is known as cinoxacin and is known to be effective against a broad spectrum of microbial organisms, as disclosed in U.S. Pat. No. 3,669,965.

Trial:

In the exemplary trial described herein, different strains of colon cancer were treated separately with a selected set of molecules. The molecule activity is scored depending on the level of activity observed. A molecule was labeled as positive for activity against a particular strain of colon cancer if its activity score is four or higher. The molecules that scored below four were entered as negative. The Mcase program was then activated for each set of positive molecules and the best molecule of each set was then tested against each of the 500 or so modules contained in the data libraries. The surviving molecules were chosen as candidates. For the purpose of this study, each biophobe that existed in the databases was used to discard all the molecules that contain them.

The trial identified six candidates, all of which are active and apparently devoid of negative side effects. Three of the candidates were found to be active against Leukemia. The other three were found active to be active against colon cancer.

Accordingly, a compound for treating, preventing, or ameliorating a hyperproliferative disease is provided. The compound is produced as a metabolite of two compounds, Formula (I) and Formula (II) disclosed in U.S. Provisional Application No. 61/288,517, fully incorporated by reference herein, or pharmaceutically acceptable salts or metabolites thereof.

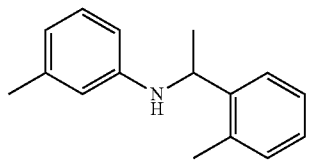

Formula (I)

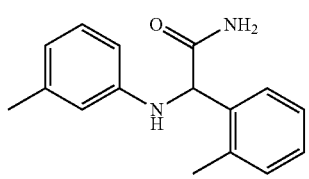

Formula (III)

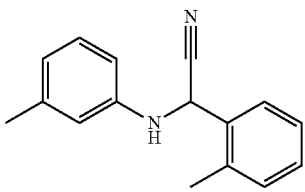

Formula (II)

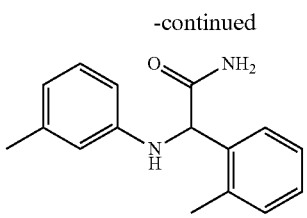

Accordingly, the subject compound, Formula (III) is prepared as a metabolite of Formula (I) and Formula (II) as illustrated below:

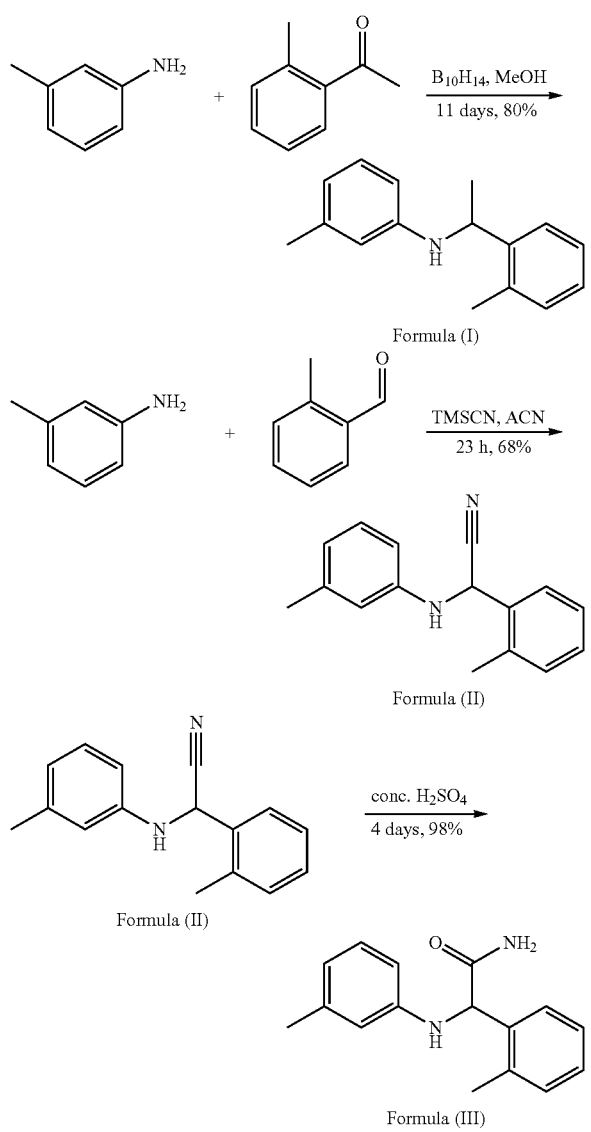

In accordance with one aspect of the present disclosure, compounds of Formula (III) or (IV), as well as a pharmaceutically acceptable salts or metabolites thereof, may be used to treat, prevent or ameliorate a hyperproliferative disease and/or disorder such as cancer. Exemplary cancers may be selected from the group consisting of cancer of the breast, bladder, bone, brain, central and peripheral nervous system, colon, endocrine glands, esophagus, endometrium, germ cells, head and neck, kidney, liver, lung, larynx and hypopharynx, mesothelioma, sarcoma, ovary, pancreas, prostate, rectum, renal, small intestine, soft tissue, testis, stomach, skin, ureter, vagina and vulva; inherited cancers, retinomblastoma and Wilms tumor; leukemia, lymphoma, non-Hodgkins disease, chronic and acute myeloid leukaemia, acute lymphoblastic leukemia, Hodgkins disease, multiple myeloma and T-cell lymphoma; myelodysplastic syndrome, plasma cell neoplasia, paraneoplastic syndromes, cancers of unknown primary site and AIDS related malignancies.

The compound of Formula (III); 2-(o-tolyl)-2-(m-tolylamino)acetamide, compounds of Formula (IV); such as cinoxacin, as well as a pharmaceutically acceptable salts or metabolites thereof may be useful for treating, preventing or ameliorating include, but are not limited to, colon cancer, leukemia, such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer, adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma basal cell carcinoma, sarcoma, and Paget's disease; cervical cancers such as but not limited to, squamous cell carcinoma, and adenocareinoma; uterine cancers such as but not limited to endometrial carcinoma and uterine sarcoma, ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoetidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, further cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagitosis, Treatment, and Recovery; Viking Penguin, Penguin Books U.S.A. Inc. United States of America).

In various exemplary embodiments, many cell lines can be subject to the method according to the present disclosure, for example, Colon Cancer such as DLD-1, COLO 205, HCC-2998, HCT-116, HCT-15, HT29, KM12, and SW-620; Leukemia such as CCRF-CEM, HL-60(TB), K-562, MOLT-4, RPMI-8226, and SR; Non-Small Cell Lung Cancer such as A549/ATCC, EKVX, HOP-62, HOP-92, NCI-H226, NCI-H23, NCI-H322M, NCI-H460, and NCI-H522; CNS Cancer such as SF-268, SF-295, SF-539, SNB-19, SNB-75, and U251; Melanoma such as LOX IMVI, MALME-3M, M14, MDA-MB-435, SK-MEL-2, SK-MEL-28, SK-MEL-5, UACC-257, and UACC-62; Ovarian Cancer such as IGROV1, OVCAR-3, OVCAR-4, OVCAR-5, OVCAR-8, NCI/ADR-RES, and SK-OV-3; Renal Cancer such as 786-0, A498, ACHN, CAKI-1, RXF 393, SN12C, TK-10, and UO-31; Prostate Cancer such as PC-3 and DU-145; Breast Cancer such as MCF7, MDA-MB-231/ATCC, HS 578T, BT-549, and T-47D.

In various exemplary embodiments, the compound of Formula (III), Formula (IV), or a pharmaceutically acceptable salt or metabolite thereof is administered as a pharmaceutical composition. Additional ingredients in the pharmaceutical composition may be selected from for example a pharmaceutically acceptable excipient, diluent and/or carrier, among others. A person skilled in the art is familiar with auxiliaries, vehicles, excipients, diluents, carriers or adjuvants which are suitable for the desired pharmaceutical formulations, preparations or compositions on account of his/her expert knowledge. For example, pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. Water is a preferred vehicle when the compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propyleneglycol, water, ethanol and the like. The present compositions, if desired, can also contain minor amounts of wetting or emulsifying agents, or pH buffering agents. In addition to solvents, gel formers, ointment bases and other active compound excipients, for example antioxidants, dispersants, emulsifiers, preservatives, solubilizers, colorants, complexing agents or permeation promoters, can be used.

In addition to the compound of Formula (III) or Formula (IV), or a pharmaceutically acceptable salt or metabolite thereof, the pharmaceutical composition may contain other therapeutic agent such as an anti-inflammatory agent. Examples of anti-inflammatory agents include, but are not limited to, steroids (e.g., cortisol cortisone, fludrocortisone, prednisone, 6a-methylprednisone, triamcinolone, betamethasone or dexamethasone), nonsteroidal antiinflammatory drugs (NSAIDS (e.g., aspirin, acetaminophen, tolmetin, ibuprofen, mefenamic acid, piroxicam, nabumetone, rofecoxib, celecoxib, etodolac or nimesulide). In another embodiment, the other therapeutic agent is an antibiotic (e.g., vancomycin, penicillin, amoxicillin, ampicillin, cefotaxime, ceftriaxone, cefixime, rifampinmetronidazole doxycycline or streptomycin). In another embodiment, the other therapeutic agent is a PDE4 inhibitor (e.g., roflumilast or rolipram). In another embodiment, the other therapeutic agent is an antihistamine (e.g., cyclizine, hydroxyzine, promethazine or diphenhydramine). In another embodiment, the other therapeutic agent is an anti-malarial (e.g., artemisinin, artemether, artsunate, chloroquine phosphate, mefloquine hydrochloride, doxycycline hyclate, proguanil hydrochloride, atovaquone or halofantrine). In one embodiment, the other therapeutic agent is drotrecogin alfa.

The term "mammal" includes an animal (e.g., cow, horse, sheep, pig, chicken, turkey, quail, cat, dog, mouse, rat, rabbit or guinea pig); a non-primate and a primate (e.g., monkey, baboon, chimpanzee and human). The compound of Formulas (III), or pharmaceutically acceptable salt or metabolite thereof may be used as human and veterinary medicine. In various embodiments, the mammal subject to the method according to the disclosure is a human patient such as an infant, child, adolescent or adult.

Without being bound by any particular theory, the present disclosure is believed to modulate apoptosis and/or aberrant cell growth in the therapy of benign or malignant neoplastic diseases, such as cancer.

The administration of the compound of Formula (III), Formula (IV), or a pharmaceutically acceptable salt or metabolite thereof may be performed in any of the generally accepted modes of administration available in the art. Illustrative examples of suitable modes of administration include intravenous, oral, nasal, parenteral, topical, transdermal and rectal delivery.

The compound of Formula (III), Formula (IV), or a pharmaceutically acceptable salt or metabolite thereof can be administered to animals (including humans) orally or parenterally in conventional and well known preparations, such as capsules, microcapsules, tablets, granules, powder, troches, pills, suppositories, injections, suspensions and syrups. Suitable formulations in this regard may be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylprrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous sicilic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrrolidone or aluminum stearate), a dispersing agent (e.g., hydroxypropylmethylcellulose), a diluent (e.g., water), and/or a base wax (e.g., cocoa buffer, white petrolatum or polyethylene glycol). The compound of Formula (1), (2), or pharmaceutically acceptable salt thereof can also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, e.g., encapsulation in liposomes, microparticles, microcapsules, capsules, etc., and can be used to administer a compound of the disclosure. Methods of administration include but are not limited to intradermal, intramuscular, intraperitoneal, intravenous, subcutaneous, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner, and will depend in-part upon the site of the medical condition. In most instances, administration will result in the release of the compound into the bloodstream.

In specific embodiments, it may be desirable to administer the compound of Formula (III), Formula (IV), or a pharmaceutically acceptable salt or metabolite thereof locally to the area in need of treatment. This can be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material including membranes, such as sialastic membranes, or fibers. In one embodiment, administration can be by direct injection at the site (or former site) of an atherosclerotic plaque tissue.

The compound of Formula (III), Formula (IV), or a pharmaceutically acceptable salt or metabolite thereof of the disclosure can be delivered in a controlled release system. In one embodiment, a pump may be used. In another embodiment, polymeric materials can be used. In an embodiment, a controlled-release system can be placed in proximity of the target of the compound, e.g., the liver, thus requiring only a fraction of the systemic dose may be used.

In an embodiment, the compound of Formula (III), Formula (IV), or a pharmaceutically acceptable salt or metabolite thereof is administered orally. Compositions for oral delivery may be in the form of tablets, lozenges, aqueous or oily suspensions, granules, powders, emulsions, capsules, syrups, or elixirs, for example. Orally administered compositions may contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the disclosure. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

In an embodiment, the compound of Formula (III), Formula (IV), or a pharmaceutically acceptable salt or metabolite thereof is administered parenterally.

In an embodiment, the compound of Formula (III), Formula (IV), or a pharmaceutically acceptable salt or metabolite thereof is administered intravenously, intramuscularly, intradermally or subcutaneously. In a preferred embodiment, the compound is formulated in accordance with routine procedures as a pharmaceutical composition adapted for intravenous administration to human beings. Typically, the compound for intravenous administration is a solution in sterile isotonic aqueous buffer. Where necessary, the composition can also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent.

In an embodiment, the compound of Formula (III), Formula (IV), or a pharmaceutically acceptable salt or metabolite thereof is administered by infusion. Where the compound is to be administered by infusion, it can be dispensed, for example, with an infusion bottle containing sterile pharmaceutical grade water or saline.

For the treatment of dermatoses, the compound of Formula (III), Formula (IV), or a pharmaceutically acceptable salt or metabolite thereof can be in particular administered in the form of those pharmaceutical compositions which are suitable for topical application. For the production of the pharmaceutical compositions, the compounds are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

Without being bound by theory, it is expected that the compound of Formula (III), Formula (IV), or a pharmaceutically acceptable salt or metabolite thereof is administered daily. However, the choice of the optimal dosage regime and duration of medication, particularly the optimal dose and manner of administration of the active compounds necessary in each case can be determined by a person skilled in the art on the basis of his/her expert knowledge. The amount of the compound of Formula (III), Formula (IV), or pharmaceutically acceptable salt or metabolite thereof in a dosage formula may differ depending on factors such as, but not limited to, the route by which it is to be administered to patients. The dosage of the disclosure can be carried out in the order of magnitude customary for inhibitors of cellular hyperproliferation or apoptosis inducers.

The compound of the disclosure may also be used in combination therapy with other active compounds. The term "combination" according to this disclosure may be present as a fixed combination, a non-fixed combination or a kit-of-parts. A "fixed combination" is defined as a combination of the compound of the disclosure and other active compounds in one unit dosage or in a single entity. One example of a "fixed combination" is a pharmaceutical composition wherein the compound of the disclosure and other active compounds are present in admixture for simultaneous administration, such as in a formulation. A "kit-of-parts" is defined as a combination wherein the compound of the disclosure and other active compounds are present in more than one unit. One example of a "kit-of-parts" is a combination wherein the compound of the disclosure and other active compounds are present separately. The components of the kit-of-parts may be administered separately, sequentially, simultaneously, concurrently or chronologically staggered.

Depending upon the particular disease to be treated or prevented, additional therapeutic active agents, which are normally administered to treat or prevent that disease, may optionally be co-administered. As used herein, additional therapeutic agents that are normally administered to treat or prevent a particular disease are known as appropriate for the disease being treated. For example, compound of the disclosure thereof may be combined with one or more known anti-cancer agents, such as e.g. with one or more chemotherapeutic and/or target specific anti-cancer agents as described below.

The compound according to this disclosure may be administered in combination therapy separately, sequentially, simultaneously, concurrently or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics, in particular art-known anti-cancer agents (chemotherapeutic and/or target specific anti-cancer agents), such as e.g. any of those mentioned above.

The compound of this disclosure exhibits inhibition of cell proliferation, i.e. they can retard the growth of and/or kill a cell contacted with that compound as compared to cells not contacted with that compound. Most preferable this inhibition of cell proliferation is 100%, meaning that proliferation of all cells is stopped and/or cells undergo programmed cell death.

The method according to the present disclosure is expected to inhibit cancer cell proliferation yet demonstrates significant absence of side effects, low toxicity, superior bioavailability in general (such as e.g. good internal absorption), superior therapeutic window, and/or further beneficial effects related with their therapeutic and pharmaceutical suitability.

Accordingly, utilizing the compounds of the present disclosure may avoid side effects from chemotherapy including, but are not limited to, gastrointestinal toxicity such as, but not limited to, early and late-forming diarrhea and flatulence; nausea; vomiting; anorexia; leukopenia; anemia; neutropenia; asthenia; abdominal cramping; fever; pain; loss of body weight; dehydration; alopecia; dyspnea; insomnia; dizziness, mucositis, xerostomia, and kidney or renal failure, as well as constipation, nerve and muscle effects, temporary or permanent damage to kidneys and bladder, flu-like symptoms, fluid retention, and temporary or permanent infertility.

The subject composition is now further described with reference to the following non-limiting example:

EXAMPLE 1

2-(o-tolyl)-2-(m-tolylamino)acetamide

Formula (II) (1 g, 4.23 mmol) was dissolved in concentrated sulfuric acid (5 mL) and stirred for four days at room temperature. The initial vibrant purple color gradually abated to become a colorless solution as the reaction went to completion. The mixture was poured into 75 mL of ice in a 150 mL beaker, stirred, and then carefully neutralized with concentrated ammonium hydroxide to pH 8. The mixture was extracted with dichloromethane, dried over anhydrous sodium sulfate, and concentrated. The crude product (Rf=0.34 in 20% ethyl acetate/hexanes) was purified by flash chromatography using ethyl acetate/hexanes and concentrated. The resulting oil was crystallized from dichloromethane/hexanes to give AAA as a white crystalline solid (1.05 g, 98% yield, m.p. 90-91.5° C.).

$^1$H NMR (400 MHz, CDCl$_3$) δ 7.38 (dt, J=7.9 Hz, 3.7H, 1H), 7.30-7.15 (3H), 7.09 (t, J=7.7 Hz, 1H), 6.78 (s, 1H), 6.69-6.60 (m, 1H), 6.54-6.40 (m, 2H), 5.94 (s, 1H), 4.95 (d, J=2.5 Hz, 1H), 4.21 (s, 1H), 2.39 (s, 3H), 2.28 (s, 3H); $^{13}$C NMR (101 MHz, CDCl$_3$) δ 175.09, 147.15 139.59, 137.18, 131.42, 129.52, 128.77, 127.01, 126.91, 120.40, 114.39, 110.88, 77.57, 77.26, 76.94, 61.03, 29.55, 21.83, 19.84.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A method for treating colon cancer in a mammal, comprising administering to said mammal a therapeutically effective amount of a compound of Formula (III) or a pharmaceutically acceptable salt thereof:

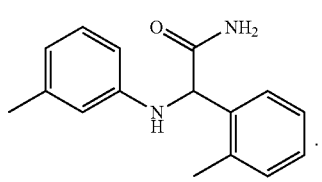

Formula (III)

2. The method of claim 1, wherein the compound or pharmaceutically acceptable salt thereof is administered as a pharmaceutical composition.

3. The method of claim 2, wherein the pharmaceutical composition further comprises a pharmaceutically acceptable excipient, diluent and/or carrier.

4. The method of claim 1, wherein the mammal is a human.

5. The method of claim 1, wherein the compound or pharmaceutically acceptable salt thereof is administered orally.

6. The method of claim 1, wherein the compound or pharmaceutically acceptable salt thereof is administered parenterally.

7. The method of claim 1, wherein the compound or pharmaceutically acceptable salt thereof is administered intravenously, intramuscularly, intradermally or subcutaneously.

8. The method of claim 1, wherein the compound or pharmaceutically acceptable salt thereof is administered by infusion.

9. The method of claim 1, wherein the compound or pharmaceutically acceptable salt thereof is administered daily.

10. The method of claim 1, wherein the compound is 2-(o-tolyl)-2-(m-tolylamino)acetamide.

11. The method of claim 1, wherein the cell line of the colon cancer is selected from the group consisting of DLD-1, COLO 205, HCC-2998, HCT-116, HCT-15, HT29, KM12, and SW-620.

* * * * *